US006251829B1

(12) United States Patent
Li et al.

(10) Patent No.: US 6,251,829 B1
(45) Date of Patent: Jun. 26, 2001

(54) HERBICIDAL BENZOYLOXY CARBOXYLATES AND CARBOXAMIDES

(75) Inventors: Bin Li; Ying Man; Zongjian Zhang; Longhe Xu, all of Liaoning (CN); Adam Chi-Tung Hsu, Lansdale, PA (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 09/551,346

(22) Filed: Apr. 18, 2000

(51) Int. Cl.$^7$ .......................... A01N 37/06; C07C 69/76; C07D 209/48; C07D 239/10
(52) U.S. Cl. .......................... 504/243; 504/227; 504/229; 504/238; 504/246; 504/248; 504/265; 504/270; 504/273; 504/280; 504/282; 504/286; 504/304; 504/315; 544/182; 544/223; 544/235; 544/236; 544/239; 544/314; 546/119; 546/121; 546/220; 548/144; 548/226; 548/263.2; 548/370.1; 548/375.1; 548/376.1; 548/476
(58) Field of Search .................................. 544/236, 314; 560/19, 20, 47; 504/243, 246, 248, 304, 315

(56) References Cited

U.S. PATENT DOCUMENTS

| 2,895,817 | 7/1959 | Luckenbaugh | 71/2.5 |
| 3,418,334 | 12/1968 | Stoffel | 260/309.5 |
| 4,283,547 | 8/1981 | Schirmer et al. | 548/307 |
| 4,985,453 | 1/1991 | Ishii et al. | 514/386 |

FOREIGN PATENT DOCUMENTS

| 53-018569 | 2/1978 | (JP) . |
| WO 93/22289 | 11/1993 | (WO) . |

OTHER PUBLICATIONS

Al–Faiyz et al., Rearrangements of Activated O–Acyl Hydroxamic Acid Derivatives, Tetrahedron Letters, vol. 39, No. 10, pp. 1269–1272, Mar. 1998.*

Dees et al., Diels–Alder Reactions of Push–Pull Olefins, Monatsh. Chem., vol. 129, No. 6/7, pp. 689–696, Jun. 1998.*

* cited by examiner

*Primary Examiner*—Richard L. Raymond
*Assistant Examiner*—Deepak R. Rao
(74) *Attorney, Agent, or Firm*—Thomas D. Rogerson

(57) ABSTRACT

This invention relates to herbicidal alpha-(2,4,5-trisubstituted)- and alpha-(2,5-disubstituted)-benzoyloxy-alpha-beta-, and/or beta-gamma-unsaturated-carboxylates and their derivatives, to compositions which contain these compounds, and to methods of use of these compounds.

10 Claims, No Drawings

HERBICIDAL BENZOYLOXY CARBOXYLATES AND CARBOXAMIDES

This invention relates to herbicidal alpha-benzoyloxy-alpha-beta-, and/or beta-gamma-unsaturated-carboxylates and their derivatives, to compositions which contain these compounds, and to methods of use of these compounds.

The presence of unwanted plant species causes substantial damage to useful crops. Prevention or minimizing the loss of a portion of such valuable crops by killing or inhibiting the growth of unwanted weeds is one way of improving this efficiency. Though many herbicides are available, the need still exists for more effective herbicides.

Alpha-beta- and beta-gamma-unsaturated carboxylic acids and their derivatives are known as agricultural herbicides (see U.S. Pat. No. 4,902,334). We have discovered that certain alpha-(2,4,5-trisubstituted)- and alpha-(2,5-disubstituted)-benzoyloxy-alpha-beta- and/or beta-gamma-unsaturated carboxylic acids and their derivatives provide superior efficacy as herbicides compared to compounds disclosed in U.S. Pat. No. 4,902,334.

The present invention, therefore, relates to such alpha-(2,4,5-trisubstituted)- and alpha-(2,5-disubstituted)-benzoyloxy-alpha-beta- and/or beta-gamma-unsaturated-carboxylates, their isomers, and agronomically acceptable salts.

We have discovered that compounds represented by formulae I and II, and their agronomically acceptable salts, are surprisingly effective as pre-emergent and post-emergent herbicides:

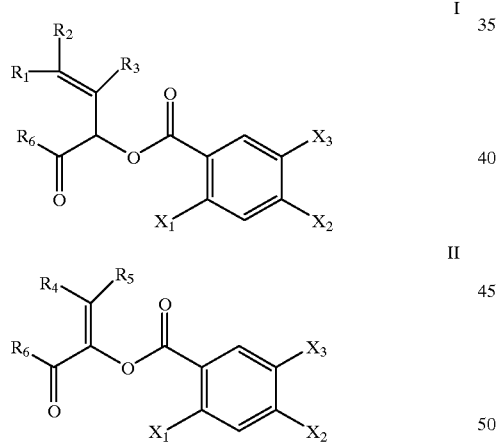

wherein
$R_1$, $R_2$, $R_3$, $R_4$, and $R_5$ are independently hydrogen, $(C_1-C_{12})$alkyl, $(C_1-C_{12})$haloalkyl, $(C_3-C_8)$cycloalkyl, $(C_2-C_8)$alkenyl, $(C_3-C_{10})$alkynyl, $(C_1-C_4)$alkoxyalkyl, $(C_3-C_8)$cycloalkoxy$(C_1-C_4)$alkyl, $(C_2-C_8)$alkenyloxy$(C_1-C_4)$alkyl, $(C_3-C_{10})$alkynyloxy$(C_1-C_4)$alkyl, $(C_1-C_{12})$alkylcarbonyl, $(C_1-C_4)$alkoxycarbonyl, $(C_2-C_8)$alkenyloxycarbonyl, cyano, $(C_1-C_{10})$alkoxy, $(C_3-C_8)$cycloalkoxy, $(C_2-C_8)$alkenyloxy, $(C_3-C_{10})$alkynyloxy, dialkylamino, $(C_1-C_{12})$alkylsulfonyl, or substituted or unsubstituted phenyl, wherein the substituents are from one to three independently selected from the group consisting of halogen, cyano, nitro, trihalomethyl, and methyl. Preferably, $R_1$, $R_2$, $R_3$, $R_4$, and $R_5$ are independently selected from hydrogen, $(C_1-C_6)$alkyl, $(C_1-C_4)$haloalkyl, $(C_4-C_5)$cyclalkyl, $(C_2-C_5)$alkenyl, $(C_3-C_6)$alkynyl, $(C_1-C_3)$alkoxy$(C_1-C_2)$alkyl, $(C_4-C6)$cycloalkoxy$(C_1-C_2)$alkyl, $(C_2-C_5)$alkenyloxy$(C_1-C_2)$alkyl, $(C_3-C_6)$alkynyloxy$(C_1-C_2)$alkyl, $(C_1-C_6)$alkylcarbonyl, $(C_1-C_4)$alkoxycarbonyl, $(C_2-C_5)$alkenyloxycarbonyl, cyano, $(C_1-C_6)$alkoxy, $(C_4-C_6)$cycloalkoxy, $(C_2-C_5)$alkenyloxy, $(C_3-C_6)$alkynyloxy, dialkylamino, $(C_1-C_6)$alkylsulfonyl or substituted or unsubstituted phenyl. More preferably, $R_1$, $R_2$, $R_3$, $R_4$, and R5 are independently selected from hydrogen, methyl, and substituted or unsubstituted phenyl, wherein the substituents are independently halogen, trihalomethyl, or methyl;

$R_6$ is $OR_7$ or $NR_8R_9$, in which $R_7$ is $(C_1-C_{12})$alkyl, $(C_2-C_{12})$alkenyl, $(C_3-C_{12})$alkynyl or aryl and $R_8$ and $R_9$ are the same or different and are hydrogen, $(C_1-C_{12})$alkyl or aryl; Preferably, $R_6$ is OEt or O-allyl.

$X_1$ is halo, or nitro. Preferably $X_1$ is chlorine, fluorine, or nitro.

$X_2$ is hydrogen, halo, halo$(C_1-C_6)$alkyl, cyano, or nitro. Preferably $X_2$ is fluorine, chlorine, trifluoromethyl, or cyano.

$X_3$ is halo, $(C_1-C_{12})$alkyl, halo$(C_1-C_{12})$alkyl, $(C_1-C_{10})$alkoxy, $(C_3-C_8)$cycloalkoxy, $(C_2-C_8)$alkenyloxy, $(C_3-C_{10})$alkynyloxy, $(C_1-C_4)$alkoxycarbonyl, $(C_2-C_8)$alkenyloxycarbonyl, $(C_3-C_{10})$alkynyloxycarbonyl, $(C_1-C_{12})$alkylsulfonylamino, $(C_1-C_{12})$alkylsulfonylalkylamino, $(C_1-C_4)$alkoxycarbonylmethoxy, $(C_1-C_4)$alkoxycarbonylethoxy, aryloxy, or Q, wherein Q is:

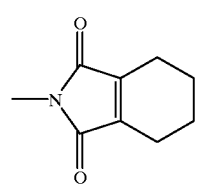

Q1

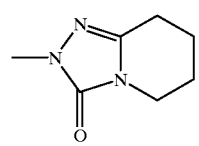

Q2

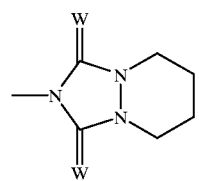

Q3

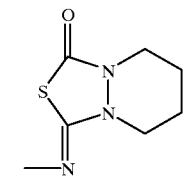

Q4

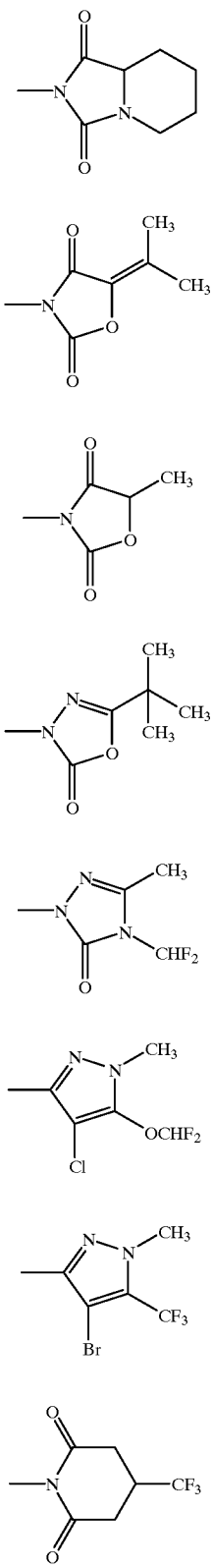
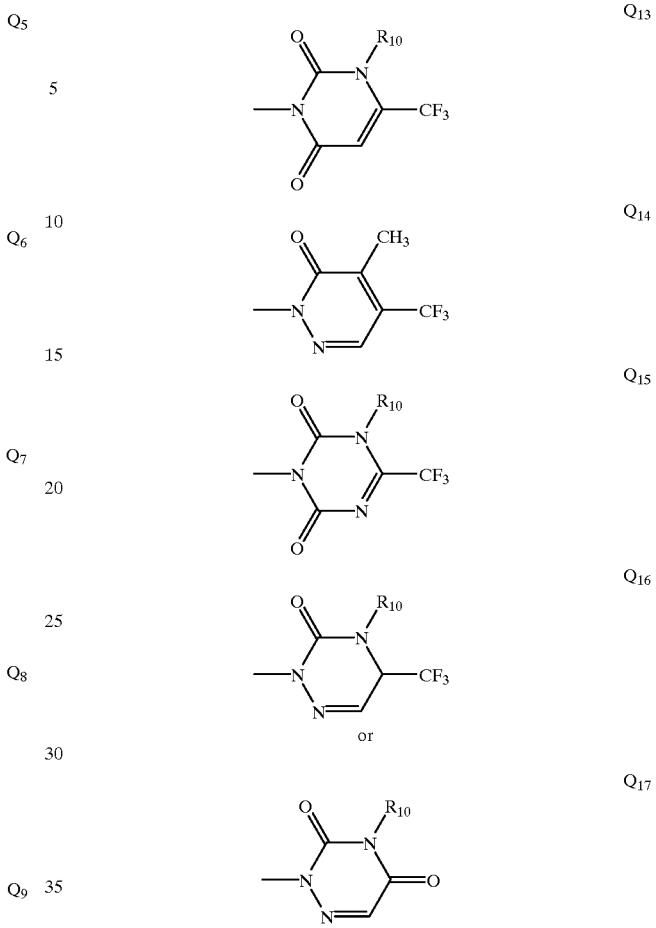

wherein W is O or S. Preferably, $X_3$ is cyclopentyloxy, 2-propynyloxy, methylsulfonylamino, methylsulfonylmethylamino, 2,4-dichlorophenoxy, 2-chloro-4-trifluromethylphenoxy, 4-trifluromethyl-2-pyridinyloxy, $Q_1$, or $Q_{13}$. $R_{10}$ is $NH_2$, OH, $(C_1–C_{10})$alkyl or substituted alkyl. Preferably, $R_{10}$ is $NH_2$, OH, or methyl.

The term "alkyl" includes both branched and straight chain alkyl groups such as, for example, methyl, ethyl, n-propyl, isopropyl, n-butyl, sec-butyl, isobutyl, tert-butyl, n-pentyl, isopentyl, n-hexyl, n-heptyl, isooctyl, nonyl, decyl, undecyl, and dodecyl. The term "cycloalkyl" refers to a cyclic aliphatic ring structure such as, for example, cyclopropane, cyclobutane, cyclopentane, cyclohexane, cycloheptane, and cyclooctane. The term "haloalkyl" refers to an alkyl group substituted with one or more halo groups. The term "halo" refers to fluoro, chloro, bromo or iodo.

The term "alkylsulfonylalkyl" refers to an alkyl group substituted with an alkylsulfonyl (alkyl-$SO_2$) group such as, for example, methylsulfonylmethyl. The term "alkylsulfinylalkyl" refers to an alkyl group substituted with an alkylsulfinyl (alkyl-SO) group such as, for example, methylsulfinylmethyl.

The term "alkenyl" refers to an ethylenically unsaturated hydrocarbon group, straight or branched, having 1 or 2 ethylenic bonds. The term "haloalkenyl" refers to an alkenyl group substituted with one or more halo groups. The term "alkynyl" refers to an unsaturated hydrocarbon group, straight or branched, having 1 or 2 acetylenic bonds.

The term "alkoxy" includes both branched and straight chain alkyl groups attached to a terminal oxygen atom. Typical alkoxy groups include, for example, methoxy, ethoxy, n-propoxy, isopropoxy, and tert-butoxy. The term "haloalkoxy" refers to an alkoxy group substituted with one or more halo groups.

The term "alkylthio" includes both branched and straight chain alkyl groups attached to a terminal sulfur atom. The term "haloalkylthio" refers to an alkylthio group substituted with one or more halo groups.

The term "aryloxy" includes phenoxy and pyridinyloxy, which may be substituted with up to three substituents selected from the group consisting of halogen, cyano, nitro, trihalomethyl, and methyl. Typical aryloxy includes, for example, 4-chlorophenoxy, 2-chlorophenoxy, 3,5-dichlorophenoxy, 2,6-dichlorophenoxy, 4-trifluoromethylphenoxy, 2-chloro-4-trifluoromethylphenoxy, 2,4,6-trichlorophenoxy, 4-trifluoromethyl-2-pyridinyloxy.

For purposes of this invention, unless otherwise specified, all percentages, parts, and ratios are by weight and all ranges are inclusive and combinable.

Agronomically acceptable salts may be formed by complexation of the compounds of the current invention with metal salts such as zinc chloride or iron chloride.

Compounds of Formula I may be prepared by reacting a compound of Formula III and a compound of Formula IV in the presence of a base in a suitable solvent at a temperature between 0 to 100° C. for 0.5 to 48 hours.

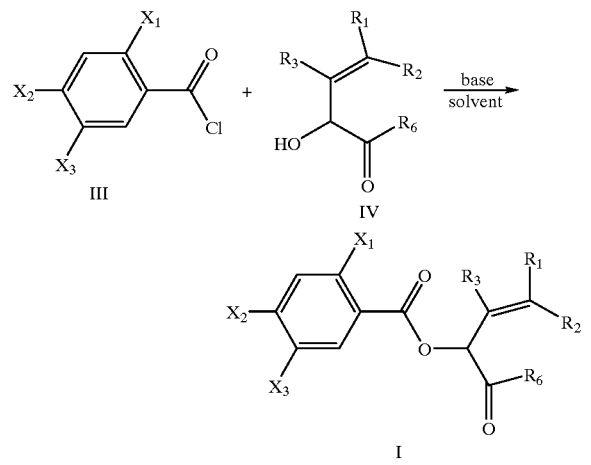

Compounds of Formula III are commercially available or can be readily prepared from benzoic acids which are commercially available or can be prepared by using known methods. Compounds of Formula IV may be prepared according to known methods (such as that in *J. Chem. Soc., Perkin Trans.* 1, (7), 1249 (1998) and *Tetrahedron Letters*, 38(34), 5917 (1997)).

Compounds of Formula II can be prepared by treating compounds of Formula I with an catalysis, such as p-toluenesulfonic acid, in a suitable solvent as depicted in the following scheme:

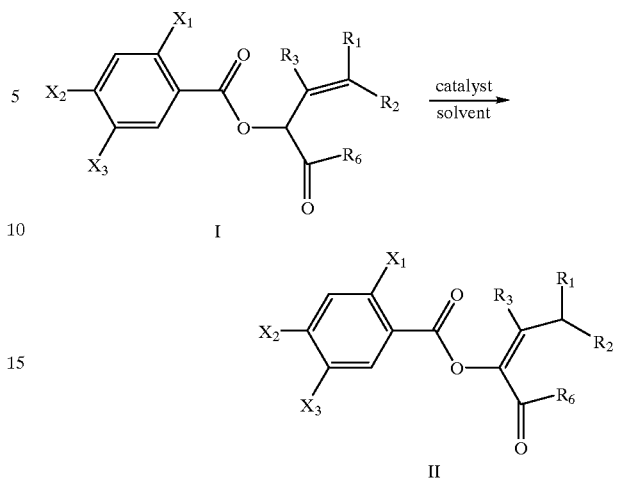

Alternatively, compounds of Formula II may be directly prepared from a benzoic acid chloride of Formula III by treating with compounds of Formula V in the presence of a base in a suitable solvent as depicted in the following scheme:

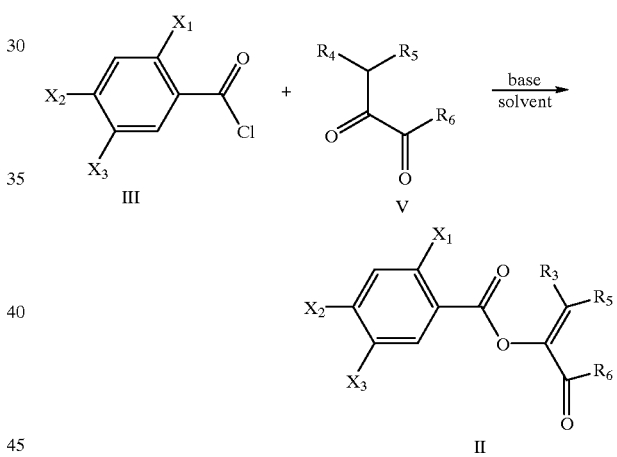

Compounds of Formula V are either commercially available or can be prepared according to known methods.

Certain compounds of Formula I may be prepared from other compounds of Formula I. For example, when $X_3$ is $NO_2$ (Formula VI), those compounds can be converted to compounds of Formula I in which $X_3$ is $NH_2$ (Formula VII) by using a reducing agent.

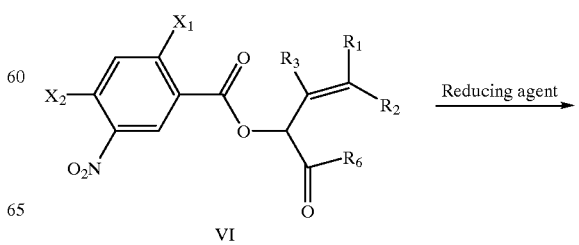

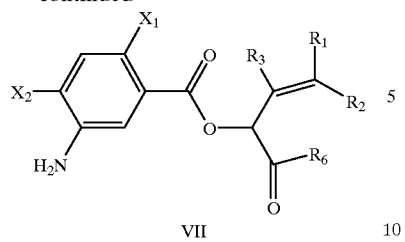

VII

In a similar manner, certain compounds of Formula II may be prepared by the chemical reaction from compounds of Formula II to other compounds of Formula II.

Occasionally, certain compounds of the Formula II may be obtained during the reaction of the compound of Formula I with another reactant in the presence of a base, preferably a stronger base such as sodium hydride, in a suitable solvent as depicted in the following scheme.

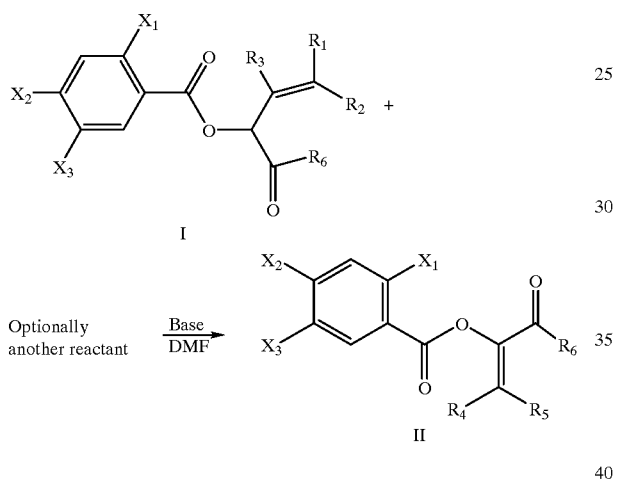

Below is a specific example which illustrates the above method.

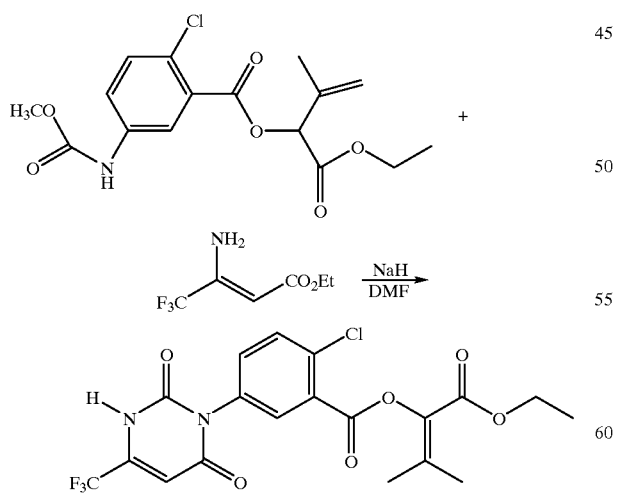

Typical compounds of Formula I and Formula II encompassed by the present invention include those compounds presented in Tables 1 and 2 below, respectively:

TABLE 1

Examples of Compounds of Formula I

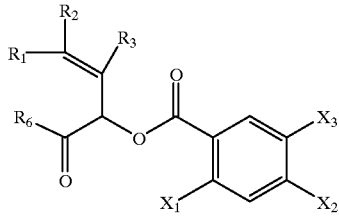

| Cmpd No | $R_1$ | $R_2$ | $R_3$ | $R_6$ | $X_1$ | $X_2$ | $X_3$ |
|---|---|---|---|---|---|---|---|
| 1 | H | H | $CH_3$ | $OC_2H_5$ | Cl | F | $NO_2$ |
| 2 | H | H | $CH_3$ | $OC_2H_5$ | Cl | F | $NH_2$ |
| 3 | H | H | $CH_3$ | $OC_2H_5$ | Cl | F | $NHCOOCH_3$ |
| 4 | H | H | $CH_3$ | $OC_2H_5$ | Cl | F | $NHCOCH_2COCF_3$ |
| 5 | H | H | $CH_3$ | $OC_2H_5$ | Cl | F | $NHCOCH=C(NH_2)CF_3$ |
| 6 | H | H | $CH_3$ | $OC_2H_5$ | Cl | H | $NO_2$ |
| 7 | H | H | $CH_3$ | $OC_2H_5$ | Cl | H | $NH_2$ |
| 8 | H | H | $CH_3$ | $OC_2H_5$ | Cl | H | $NHCOOCH_3$ |
| 9 | H | H | $CH_3$ | $OC_2H_5$ | Cl | F | $Q_1$ |
| 10 | H | H | $CH_3$ | $OC_2H_5$ | Cl | F | $Q_{13}(R_{10}=H)$ |
| 11 | H | H | $CH_3$ | $OC_2H_5$ | Cl | F | $Q_{13}(R_{10}=CH_3)$ |
| 12 | H | H | $CH_3$ | $OC_2H_5$ | Cl | H | $Q_3(W=O)$ |
| 13 | H | H | $CH_3$ | $OC_2H_5$ | Cl | H | $Q_4$ |
| 13a | H | H | $CH_3$ | $OC_2H_5$ | $NO_2$ | H | 2-Cl-4-$CF_3$-phenoxy- |

TABLE 2

Examples of Formula II

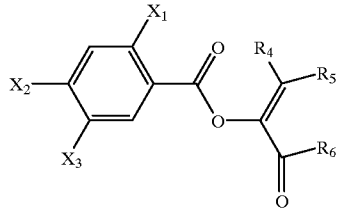

| Cmpd No | $R_4$ | $R_5$ | $R_6$ | $X_1$ | $X_2$ | $X_3$ |
|---|---|---|---|---|---|---|
| 14 | $CH_3$ | $CH_3$ | $OC_2H_5$ | Cl | F | $NO_2$ |
| 15 | $CH_3$ | $CH_3$ | $OC_2H_5$ | Cl | H | $Q_{13}(R_{10}=H)$ |
| 16 | $CH_3$ | $CH_3$ | $OC_2H_5$ | Cl | H | $Q_{13}(R_{10}=CH_3)$ |
| 17 | $CH_3$ | $CH_3$ | $OC_2H_5$ | $NO_2$ | H | $(2Cl,4CF_3)C_6H_3O$ |

EXAMPLES

Preparation of Compound No. 1

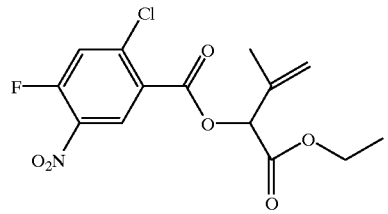

Oxalyl chloride (12.7 g, 100 mmoles) was added to a solution of 2-chloro-4-fluoro-5-nitrobenzoic acid (17.6 g, 80 mmoles) in methylene chloride (150 mL) containing a few drops of dimethylformamide (DMF) with stirring in an ice water bath. The reaction mixture was stirred at room temperature overnight. The solution was concentrated on a rotary evaporator to give 2-chloro-4-fluoro-4-nitrobenzoyl chloride as an oily product yielding 19.2 g, which was used for the next step without further purification.

A solution of 2-chloro-4-fluoro-4-nitrobenzoyl chloride (19.2 g, 80.7 mmoles) in methylene chloride (50 mL) was added dropwise to a solution of ethyl 2-hydroxy-3-methyl-3-butenoate (17g, 70%, 83 mmoles) in methylene chloride (100 mL) containing triethylamine (10.1 g, 100 mmoles) in an ice water bath. The mixture was stirred at 0 to 5° C. for 2 hr and then at room temperature for another 3 hr. The solution was concentrated under reduced pressure to give a residue. The residue was treated with ethyl acetate and washed sequentially with water, 10% potassium carbonate, water and brine; dried over MgSO$_4$; and filtered. Evaporation of solvent to give ethyl 2-[(2-chloro-4-fluoro-5-nitrobenzoyl)oxy]-3-methyl-3-butenoate as an oily product, 25 g (yield=89.7%). An $^1$H nmr (CDCl$_3$) showed the desired structure: δ 8.74 (d, 1H), 7.48 (d, 1H), 5.64 (s, 1H), 5.32 (s, 1H), 5.22 (s, 1H), 4.25 (q, 2H), 1.91 (s, 3H), 1.27 (t, 3H).

Preparation of Compound No. 2

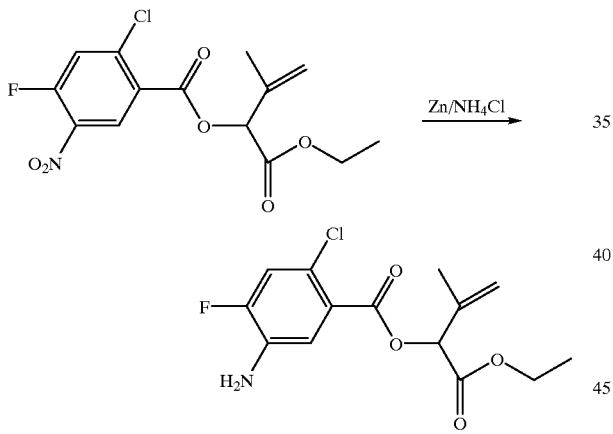

Ethyl 2-(2-chloro-4-fluoro-5-nitrobenzoyl)oxy-3-methyl-3-butenoate (3.5 g, 10.13 mmoles) was added to a mixture of 2N NH$_4$Cl (80 mL) in tetrahydrofuran (THF) (100 mL) at room temperature. The above mixture was cooled in an ice cold water bath and zinc dust (1.4 g, 21.4 mmoles) was added. The mixture was then stirred at room temperature for 2 hrs. The solid was removed by suction-filtration and the filtrate was concentrated under reduced pressure to give a black oily product. The crude product was subjected to a column silica gel chromatography and eluted with EtOAc/hexane (1:4) to give ethyl 2-(2-chloro-4-fluoro-5-aminobenzoyl)oxy-3-methyl-3-butenoate, 0.5 g (yield =45.6%), as an oily product. An $^1$H nmr (CDCl$_3$) showed the desired product: δ 7.42 (d, 1H), 7.11 (d, 1H), 5.60 (s, 1H), 5.29 (s, 1H), 5.17 (s, 1H), 4.25 (q, 2H), 3.90 (br, 2H), 1.91 (s, 3H), 1.29 (t, 3H).

Preparation of Compound No. 8

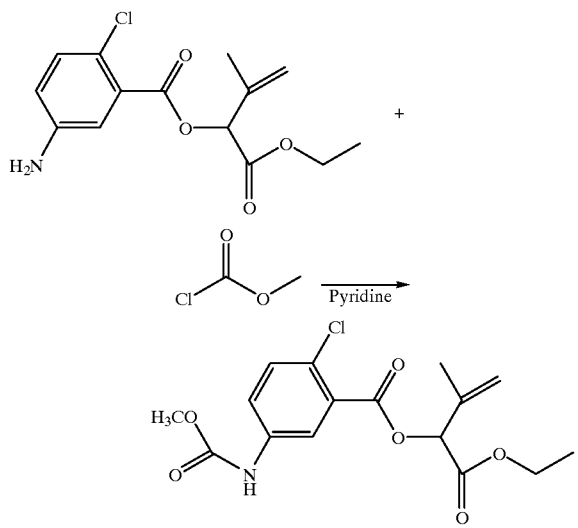

Pyridine (0.4 mL, 5 mmoles) was added to a solution of ethyl 2-(2-chloro-5-aminobenzoyl)oxy-3-methyl-3-butenoate (1.5 g, 5 mmoles) in methylene chloride (50 mL) at 0 to 5° C. with magnetic stirring. A solution of methyl chloroformate (0.5 g, 5 mmoles) in methylene chloride (10 mL) was then added over 30 min. The mixture was stirred at room temperatureroom temperature for 4 hrs. The mixture was diluted with methylene chloride and washed with 4% HCl and then water. The organic layer was dried over MgSO$_4$ and filtered and concentrated under reduced pressure to give 2-[2-chloro-5-(methoxycarbonyl)amino]-benzoyloxy-3-methyl-3-butenoate (compound No.9), 1.4 g, as an oily product. An $^1$H nmr (CDCl$_3$) showed the desired product: δ 7.85 (s, 1H), 7.65 (m, 1H), 7.39 (m, 1H), 6.92 (s, 1H), 5.62 (s, 1H), 5.30 (s, 1H), 5.18 (s, 1H), 4.26 (q, 2H), 3.78 (s, 3H), 1.90 (d, 3H), 1.30 (t, 3H).

The Preparation of Compound No.12

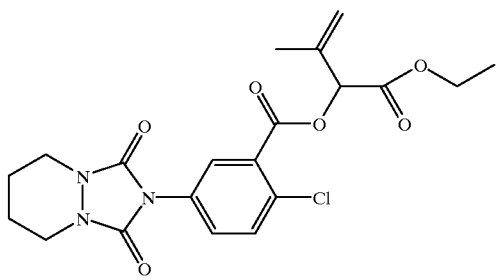

Procedure:
NaOH solution (50%, 0.8 g, 10 mmoles), followed by ethyl 2-(2-chloro-5-isocyanatobenzoyl)oxy-3-methyl-3-butenoate (0.65 g, 2 mmoles), were added to a solution of perhydropyridazine dihydrochloride (0.65 g, 4 mmoles) in THF (15 mL) and water (10 mL). The reaction mixture was stirred at room temperature for 2 hrs. The mixture was diluted with ethyl acetate (100 mL) and washed sequentially with water, saturated NaHCO$_3$ solution, 2N HCl, sat'd NaHCO$_3$ solution, and brine. Dried over MgSO$_4$ and filtered. Evaporation of solvents gave ethyl 2-{2-chloro-5-[tetrahydro-1(2H)-pyridazinecarbonylamino]}-benzoyoxy-3-methyl-3-butenoate (0.52 g) as an oil. An $^1$H nmr (CDCl$_3$) showed the desired compound: δ 8.68 (s, 1H), 7.90 (m, 1H), 7.80 (s, 1H), 7.35 (d, 1H), 7.25 (s, 1H), 5.60 (s, 1H), 5.30 (s, 1H), 5.17 (s, 1H), 4.25 (q, 2H), 3,41 (br s, 2H), 2.95 (br s, 2H), 1.90 (s, 3H), 1.68 (m, 4H), 1.25 (t, 3H).

Triethyl amine (0.3 mL, 2.2 mmoles) was added to a solution of ethyl 2-{2-chloro-5-[tetrahydro-1(2H)-pyridazinecarbonylamino]}benzoyoxy-3-methyl-3-butenoate (0.50 g, 1.2 mmoles) in methylene chloride (20 mL). The mixture was cooled to 0 to 5° C. in an ice water bath. To the above mixture was slowly added a solution of phosgene (0.7 mL of 1.93 M toluene solution, 1.3 mmoles) in methylene chloride (8 mL). The reaction mixture was stirred at room temperatureroom temperature for 2 hr. The mixture was diluted with methylene chloride (80 mL) and washed sequentially with water, saturated NaHCO$_3$, and brine dried over Na$_2$SO$_4$, and filtered. Evaporation of solvents gave a black oil. A purer product was obtained by column chromatography on silica gel, eluted with ethyl acetate/hexane (1:4) to give ethyl 2-{2-chloro-5-(tetrahydro-1,3-dioxo-1H-[1,2,4]triazolo[1,2-a]pyridazin-2(3H)-yl)}-benzoyloxy-3-methyl-3-butenoate (0.2 g) as an oil. An $^1$H nmr (CDCl$_3$) showed the desired product: δ 8.22 (s, 1H), 7.70 (d, 1H), 7.54 (d, 1H), 5.62 (s, 1H), 5.30 (s, 1H), 5.17 (s, 1H), 4.26 (q, 2H), 3.62 (br s, 4H), 1.90 (s, 3H), 1.86 (m 4H), 1.27 (t, 3H).

Preparation of Compound No. 14

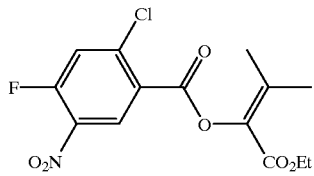

2-chloro-4-fluoro-5-nitrobenzoyl chloride (2.38 g, 10 mmoles) was added to a solution of ethyl 3-methyl-2-oxobutyrate (1.44 g, 10 mmoles) and triethylamine (1.01 g, 10 mmoles) in methylene chloride (20 mL) with stirring at room temperatureroom temperature. The mixture was stirred at room temperature overnight. The mixture was diluted with methylene chloride and washed sequentially with water, 10% HCl, water, and brine, dried over Na$_2$SO$_4$, and filtered. Evaporation of solvents gave ethyl 2-(2-chloro-4-fluoro-5-nitro)benzoyloxy-3-methyl-2-butenoate (2.41 g) as an oily product. An $^1$H nmr (CDCl3) showed the desired product: δ 8.80 (d, 1H), 7.51 (d, 1H), 4.24 (q, 2H), 2.30 (s, 3H), 1.91 (s, 3H), 1.27 (t, 3H).

Preparation of Compound No. 15

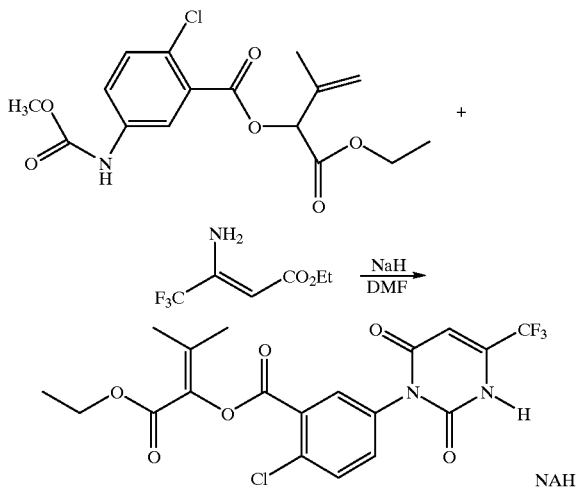

(0.2 g, 60% in mineral, 5 mmoles) was added in a few portions to a solution of ethyl 3-amino-4,4,4-trifluorocrotonate (0.9 g, 5 mmoles) in DMF (20 mL) at 0 to 5° C. with magnetic stirring. The mixture was stirred at room temperature for 20 min. To the above mixture was dropwise added a solution of ethyl 2-[2-chloro-5-(methoxycarbonyl)amino]-benzoyloxy-3-methyl-3-butenoate (1.4 g, 4 mmoles) in DMF (10 mL). The resulting black solution was heated at 100° C. for 4 hrs. The mixture was cooled to room temperature and was diluted with ethyl acetate. The solution was washed sequentially with water and brine. The organic layer was dried over MgSO4 and filtered. Evaporation of solvent gave ethyl 2-{2-chloro-5-[3,6-dihydro-2,6-dioxo-4-(trifluoromethyl)-1(2H)-pyrimidinyl]}bezoyloxy-3-methyl-2-butenoate, 0.8 g, as an oily product. An 1H nmr (CDCl$_3$) showed the desired compound: δ 7.92 (s, 1H), 7.64 (d, 1H), 7.32 (m, 1H), 6.25 (s, 1H), 6.18 (BS, 1H), 4.20 (m, 2H), 2.08 (s, 3H), 1.90 (s, 3H), 1.26 (t, 3H).

Preparation of Compound No. 16

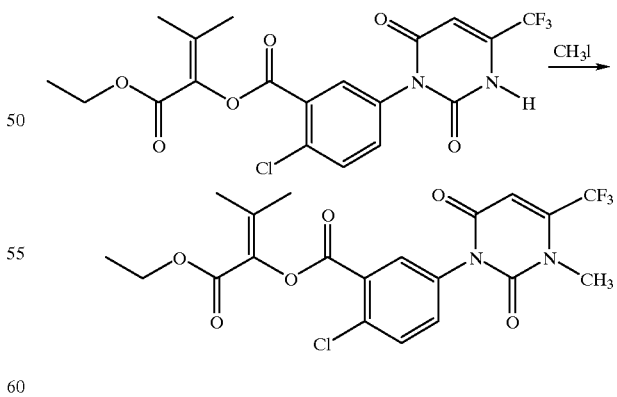

Iodomethane (0.5 mL, excess) was added to a mixture of ethyl 2-{2-chloro-5-[3,6-dihydro-2,6-dioxo-4-(trifluoromethyl)-1(2H)-pyrimidinyl]}bezoyloxy-3-methyl-2-butenoate (0.8 g, 1.7 mmoles) and potassium carbonate (0.28 g, mmoles) in acetone (15 mL). The mixture was stirred at room temperature overnight. The mixture was treated with water and extracted with ethyl acetate. The organic layer was washed with water and brine, dried over Na$_2$SO$_4$, and filtered. Evaporation of solvent gave 0.3 g crude product. Purification by column chromatography on silica gel, eluted with EtOAc/hexane (1:4), gave ethyl 2-{2-chloro-5-[3,6-dihydro-3-methyl-2,6-dioxo-4-(trifluoromethyl)-1(2H)-pyrimidinyl]}bezoyloxy-3-methyl-2-butenoate (0.20 g) as an oily product, which solidified after standing, m.p. 123–125° C. An $^1$H nmr (CDCl3) showed the desired product: δ 7.91 (s, 1H), 7.65 (d, 1H), 7.32 (m, 2H), 6.35 (s, 1H), 4.20 (m, 2H), 3.52 (s, 3H), 2.25 (s, 3H), 1.85 (s, 3H), 1.26 (t, 3H).

Preparation of Compound No. 17

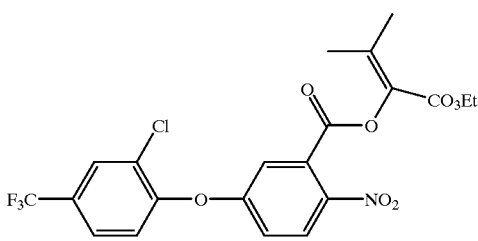

Oxalyl chloride (5.2 g, 41.4 mmoles), followed by a few drops of DMF, was added to a solution of 2-nitro-5-(2-chloro-4-trifluoromethyl)phenoxy benzoic acid (10 g, 27.6 mmoles) in methylene chloride (100 mL) at 0 to 5° C. with magnetic stirring. The mixture was stirred in an ice water bath for 5 hrs. The solvents were evaporated on a rotary evaporator to give 2-nitro-5-(2-chloro-4-trifluoromethyl) phenoxy benzoic acid chloride which was used in the next step without further purification.

2-Nitro-5-(2-chloro-4-trifluoromethyl)phenoxy benzoic acid chloride (0.80 g, 2.5 mmoles) was added to a solution of ethyl 3-methyl-2-oxobutyrate (0.35 mL, d=0.989, 2.5 mmoles) and triethylamine (0.35 mL, d=0.726, 2.5 mmoles) in methylene chloride (20 mL) at room temperature. The mixture was stirred at room temperature overnight. The mixture was diluted with methylene chloride and washed sequentially with water, 10% HCl, water, and brine, dried over Na$_2$SO$_4$, and filtered. Evaporation of solvents gave ethyl 2-{2-nitro-5-[(2-chloro-4-trifluoromethyl)phenoxy]-benzoyl)oxy}-3-methyl-2-butenoate, 0.12 g as an oily product. An $^1$H nmr (CDCl$_3$) showed the desired compound: δ 8.11 (d, 1H), 7.82 (s, 1H), 7.60 (d, 1H), 7.32 (m, 2H), 7.10 (m, 1H), 4.18 (q, 2H), 2.27 (s, 3H) 1.97 (s, 3H), 1.18 (t, 3H).

Additional NMR data are provided for the compounds listed in Table 1 and Table 2.

Compound No. 1H NMR (CDCl3), TMS=0 ppm 3 8.78 (d, 1H), 7.25 (m, 2H), 5.60 (s, 1H), 5.30 (s, 1H), 5.18 (s, 1H), 4.26 (q, 2H), 3.82 (s, 3H), 1.94 (s, 3H), 0.90 (t, 3H)

4 13.14 (br s, 1H), 8.94 (d, 1H), 7.90 (s, 1H), 7.20 (d, 1H), 5.75–5.16 (m, 4H), 4.29 (q, 2H), 1.92 (s, 3H), 1.33 (t, 3H)

5 9.05 (d, 1H), 7.21 (m, 2H), 6.50 (br s, 2H), 5.60 (s, 1H), 5.32 (s, 1H), 5.16 (d, 2H), 4.27 (q, 2H), 1.92 (s, 3H), 1.30 (t, 3H)

6 8.80 (s, 1H), 8.30 (d, 1H), 7.68 (d, 1H), 5.66 (s, 1H), 5.33 (s, 1H), 5.22 (s, 1H), 4.28 (q, 2H), 1.92 (s, 3H), 1.29 (t, 3H)

7 7.26 (m, 2H), 6.75 (d, 1H), 5.60 (s, 1H), 5.30 (s, 1H), 5.17 (s, 1H), 4.25 (q, 2H), 3.80 (br s, 2H), 1.90 (s, 3H), 1.27 (t, 3H)

9 1.95 (d, 1H), 1.38 (d, 1H), 5.61 (s, 1H), 5.29 (s, 1H), 5.17 (s, 1H), 4.25 (q, 2H), 2.43 (m, 4H), 1.86 (s, 3H), 1.83 (m, 4H), 1.29 (t, 3H)

10 8.80 (br s, 1H), 7.96 (d, 1H), 7.40 (d, 1H), 6.24 (s, 1H), 5.61 (s, 1H), 5.28 (s, 1H), 5.17 (s, 1H), 4.24 (q, 2H), 1.88 (s, 3H), 1.29 (t, 3H)

11 7.96 (d, 1H), 7.40 (d, 1H), 6.38 (s, 1H), 6.60 (s, 1H), 5.28 (s, 1H), 5.16 (s, 1H), 4.25 (q, 2H), 3.57 (s, 3H), 1.87 (s, 3H), 1.29 (t, 3H)

13a 8.01–7.10 (m, 6H), 5.58 (s, 1H), 5.25 (s, 1H), 5.13 (s, 1H), 4.20 (q, 2H), 1.81 (s, 3H), 1.22 (t, 3H)

Herbicidal Activity:

The compounds of Formulae I and II are useful as active ingredients for herbicides. When the compound of Formulae I and II of the present invention is used as a herbicide, the active ingredient can be used in a suitable formulation depending upon the particular purpose and by a suitable application method. Usually, the active ingredient is diluted with an inert liquid or solid carrier, and used in the form of a formulation such as a dust, a wettable powder, an emulsifiable concentrate, aqueous or oil suspension, pellets, granules, etc., If desirable may also add a surfactant and/or other additive. Furthermore, one of ordinary skill in the art will recognize that the compound of the present invention may be used in combination with an insecticide, a nematocide, a fungicide, other herbicides, a plant growth controlling agent, a fertilizer, and similar materials. In use, unwanted vegetation is controlled by applying to the vegetation, or to the soil wherein the unwanted vegetation grows, an herbicidally effective amount of a compound of Formula I or II or a composition comprising one or more compounds of Formula I or II and an agronomically acceptable carrier.

The compounds of the present invention can be used in the form of compositions or formulations. Examples of the preparation of compositions and formulations can be found in the American Chemical Society publication "Pesticidal Formulation Research," (1969), Advances in Chemistry Series No. 86, written by Wade Van Valkenburg; and the Marcel Dekker, Inc. publication "Pesticide Formulations", (1973) edited by Wade Van Valkenburg. In these compositions and formulations, the active substance is mixed with conventional inert agronomically acceptable (i.e., plant compatible and/or pesticidally inert) pesticide diluents or extenders such as solid carrier material or liquid carrier material, of the type usable in conventional pesticide compositions or formulations. By "agronomically acceptable carrier" is meant any substance which can be used to dissolve, disperse of diffuse the active ingredient in the composition without impairing the active ingredient's effectiveness and which by itself has no significant detrimental effect on the soil, equipment, desirable plants, or agronomic environment. Optionally, additional adjuvants may be incorporated into the composition including, for example, additional wetting agents (e. g., surfactants), spreading agents, additional dispersing agents, stickers, adhesives, processing aids (e. g., antifoaming agents), antifreeze agents (e. g., glycols such as ethylene, propylene, and dipropylene glycol), buffers, additional thickeners, and stabilizers (e. g., inorganic salts). Such adjuvants commonly used in the art can be found in McCutcheon's Emulsifiers and Detergents, McCutcheon's Emulsifiers and Detergents/Functional Materials and McCutcheon's Functional Materials all published annually by McCutcheon Division of MC Publishing Company (New Jersey, USA) or *Detergents and Emulsifiers, Annual*, (Allured Publishing Company, Ridgewood, N.J., USA). Compositions and formulations according to the present invention may also include known pesticidal compounds. This expands the spectrum of activity of the preparation and may give rise to synergism. Such formulations, contain from about 0.1% to 99.9% by weight of active ingredient(s) and at least one of (a) about 0.1% to 20% surfactant(s) and (b) about 1% to 99.9% solid or liquid diluent(s).

If the compounds of Formula I or II are formulated with an additional herbicide, the concentration of active ingredient(s) in the compositions can vary within a wide range, depending on the active compound, the applications for which they are destined, the environmental conditions and the kind of formulation. The total concentration of active ingredient(s) in the compositions is generally between 1% to 95%, preferably between 5% to 60%.

The effective dose of the compounds of the present invention is usually within a range of from 10 g/ha to 3 kg/ha, preferably from 50 g/ha to 500 g/ha. The compositions of this invention can be diluted or applied as is to plant foliage and/or soil as aqueous sprays by methods commonly employed, such as conventional high-volume hydraulic sprays, low-volume sprays, air-blast, and aerial sprays. The dilution and rate of application will depend upon the type of equipment employed, the method and frequency of application desired, the fungicide application rate, and the fungi to be controlled. The compositions can be mixed with fertilizers or fertilizing materials before their application.

Biological Testing:

Listed below, a typical planting design for the test, consisting in four monocot weeds, four dicot weeds and one sedge weed.

| Common Name | Scientific Name |
|---|---|
| Grasses | |
| Barnyardgrass | *Echinochloa crusgalli* |
| Crabgrass (large) | *Digitaria sanguinalis* |

-continued

| Common Name | Scientific Name |
|---|---|
| Foxtail, (green) | *Setaria viridis* |
| Perennial Ryegrass | *Lolium perenne* |
| Sedges | |
| Nutsedge, (yellow) | *Cyperus esculentus* |
| Broad Leaf Weeds | |
| Hairy Beggarticks | *Bidens pilosa* |
| Nightshade, (black) | *Solanum nigrum* |
| Smartweed, (pale) | *Polygonum lapathifolium* |
| Velvetleaf | *Abutilon theophrasti* |

For each compounds, the evaluation tests were carried out according to the following operating procedures.

For preemergence tests, immediately after planting, the test compound was sprayed directly onto the soil surface. The flats or pots were placed in the greenhouse and then watered. For postemergence tests, the seeds were allowed to germinate and grow for 10 to 21 days before application. The test plants were selected for uniformity, size, and stage of development. The test plants were then treated with the test compound, returned to the greenhouse and watered. Untreated control plants were used as a comparison.

The compound to be evaluated was dissolved in an appropriate solvent, usually acetone, or a formulation as described above was added to the water, and sprayed over the flats or pots using a carrier volume equivalent to 187 or 468 liters per hectare at the rate of application in grams per hectare (g/ha). Between two to four weeks after application of the test compounds, the state of the plant was observed. Each species was evaluated on a scale of 0–100 in which 0 equals no activity and 100 equals total control. Test results are shown in Tables 3 and 4.

TABLE 3

Pre-emergence Test Results

| Cpd No. | Dose (g/ha) | BID | NS | SMT | VEL | BYG | CRB | FOX | NUT | RYE |
|---|---|---|---|---|---|---|---|---|---|---|
| 9 | 1200 | 100 | 100 | 95 | 80 | 30 | 95 | 100 | 0 | 0 |
| 16 | 1200 | 100 | 100 | 100 | 100 | 100 | 100 | 100 | 98 | 100 |
| 13a | 1200 | 100 | 100 | 75 | 75 | 40 | 100 | 100 | 0 | 20 |

TABLE 4

Pre-emergence Test Results

| Cpd Cmpd. No. | Dose (g/ha) | BID | NS | SMT | VEL | BYG | CRB | FOX | NUT | RYE |
|---|---|---|---|---|---|---|---|---|---|---|
| | | | | | | Post-emergence | | | | |
| 9 | 1200 | 100 | 100 | 100 | 100 | 80 | 0 | 80 | 30 | 40 |
| 11 | 300 | 90 | 95 | 95 | 100 | 75 | 20 | 30 | 25 | 20 |
| 12 | 1200 | 80 | 80 | 80 | 100 | 40 | 40 | 40 | 40 | 40 |
| 16 | 1200 | 100 | 100 | 100 | 100 | 100 | 100 | 100 | 90 | 95 |
| 13a | 1200 | 95 | 95 | 80 | 100 | 100 | 95 | 90 | 40 | 30 |

We claim:

1. A compound of formula I or II:

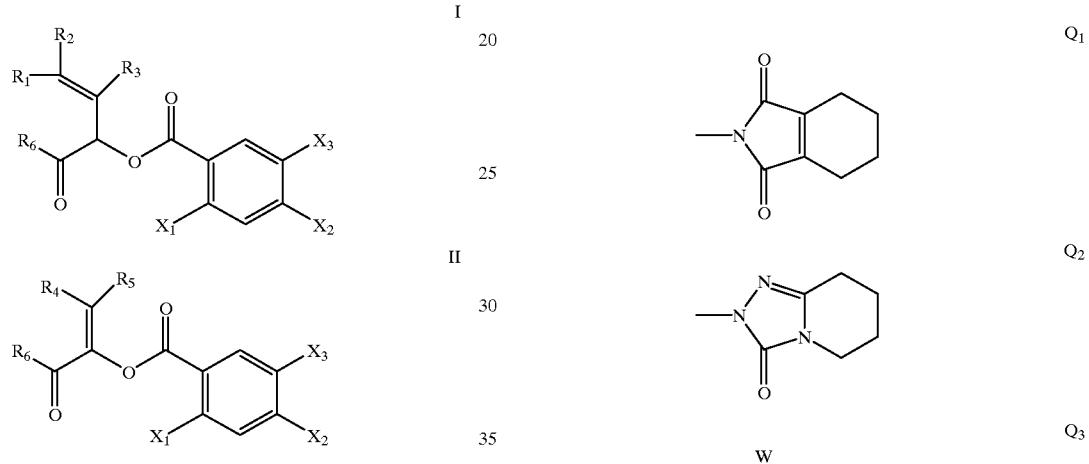

wherein $R_1$, $R_2$, $R_3$, $R_4$, and $R_5$ are independently hydrogen, $(C_1-C_{12})$alkyl, $(C_1-C_{12})$haloalkyl, $(C_3-C_8)$cycloalkyl, $(C_2-C_8)$alkenyl, $(C_3-C_{10})$alkynyl, $(C_1-C_4)$alkoxyalkyl, $(C_3-C_8)$cycloalkoxy$(C_1-C_4)$alkyl, $(C_2-C_8)$alkenyloxy$(C_1-C_4)$alkyl, $(C_3-C_{10})$alkynyloxy $(C_1-C_4)$alkyl, $(C_1-C_{12})$alkylcarbonyl, $(C_1-C_4)$ alkoxycarbonyl, $(C_2-C_8)$alkenyloxycarbonyl, cyano, $(C_1-C_{10})$alkoxy, $(C_3-C_8)$cycloalkoxy, $(C_2-C_8)$ alkenyloxy, $(C_3-C_{10})$alkynyloxy, dialkylamino, $(C_1-C_{12})$alkylsulfonyl, or substituted or unsubstituted phenyl, wherein the substituents are from one to three independently selected from the group consisting of halogen, cyano, nitro, trihalomethyl, and methyl;

$R_6$ is $OR_7$ or $NR_8R_9$, in which $R_7$ is $(C_1-C_{12})$alkyl or aryl and $R_9$ and $R_9$ are the same or different and are hydrogen, $(C_1-C_{12})$alkyl or aryl;

$X_1$ is hydrogen, halo, or nitro $X_2$ is halo, halo$(C_1-C_6)$alkyl, cyano, or nitro;

$X_3$ is halo, $(C_1-C_{12})$alkyl, halo$(C_1-C_{12})$alkyl, $(C_1-C_{10})$ alkoxy, $(C_3-C_8)$cycloalkoxy, $(C_2-C_8)$alkenyloxy, $(C_3-C_{10})$alkynyloxy, $(C_1-C_4)$alkoxycarbonyl, $(C_2-C_8)$ alkenyloxycarbonyl, $(C_3-C_{10})$alkynyloxycarbonyl, $(C_1-C_{12})$alkylsulfonylamino, $(C_1-C_{12})$ alkylsulfonylalkylamino, $(C_1-C_4)$ alkoxycarbonylmethoxy, $(C_1-C_4)$ alkoxycarbonylethoxy, aryloxy, or Q, wherein Q is:

-continued

Q7 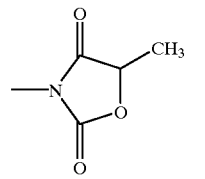

Q8 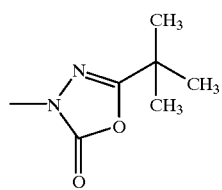

Q9 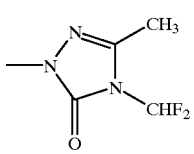

Q10 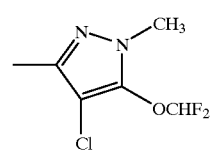

Q11 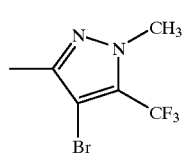

Q12 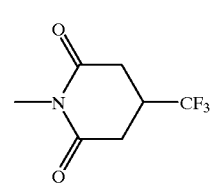

Q13 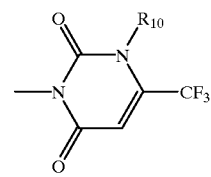

Q14 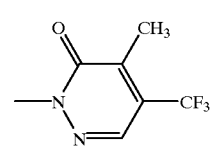

Q15 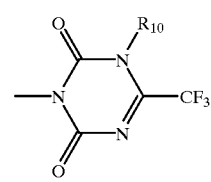

Q16 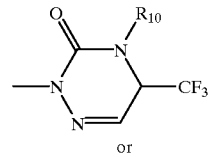

or

Q17 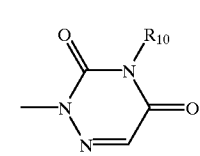

and wherein W is O or S; and $R_{10}$ is $NH_2$, OH, $(C_1-C_{10})$alkyl or substituted alkyl;

and agronomically acceptable salts thereof.

2. The compound of claim 1, wherein:

$R_1$, $R_2$, $R_3$, $R_4$, and $R_5$ are independently selected from hydrogen, $(C_1-C_6)$alkyl, $(C_1-C_4)$haloalkyl, $(C_4-C_5)$ cyclalkyl, $(C_2-C_5)$alkenyl, $(C_3-C_6)$alkynyl, $(C_1-C_3)$ alkoxy$(C_1-C_2)$alkyl, $(C_4-C_6)$cycloalkoxy$(C_1-C_2)$ alkyl, $(C_2-C_5)$alkenyloxy$(C_1-C_2)$alkyl, $(C_3-C_6)$ alkynyloxy$(C_1-C_2)$alkyl, $(C_1-C_6)$alkylcarbonyl, $(C_1-C_4)$alkoxycarbonyl, $(C_2-C_5)$alkenyloxycarbonyl, cyano, $(C_1-C_6)$alkoxy, $(C4-C_6)$cycloalkoxy, $(C_2-C_5)$ alkenyloxy, $(C_3-C_6)$alkynyloxy, dialkylamino, $(C_1-C_6)$ alkylsulfonyl or phenyl.

3. The compound of claim 2, wherein $R_1$, $R_2$, $R_3$, $R_4$, and $R_5$ are independently selected from hydrogen, methyl, and phenyl.

4. The compound of claim 1, wherein $R_6$ is OEt.

5. The compound of claim 1, wherein $X_1$ is chlorine, fluorine, or nitro.

6. The compound of claim 1, wherein $X_2$ is fluorine, chlorine, trifluoromethyl, or cyano.

7. The compound of claim 1, wherein $X_3$ is cyclopentyloxy, 2-propynyloxy, methylsulfonylamino, methylsulfonylmethylamino, 2,4-dichlorophenoxy, 2-chloro-4-trifluromethylphenoxy, 4-trifluromethyl-2-pyridinyloxy, $Q_1$, or $Q_{13}$.

8. The compound of claim 1, wherein $R_{10}$ is $NH_2$, OH, or methyl.

9. A herbicidal composition comprising one or more compounds of claim 1 and an agronomically acceptable carrier.

10. A method of controlling unwanted vegetation comprising applying to the vegetation, or to the soil wherein the unwanted vegetation grows, a herbicidally effective amount of the composition of claim 9.

* * * * *